United States Patent
Nagrath et al.

(10) Patent No.: US 12,053,569 B2
(45) Date of Patent: Aug. 6, 2024

(54) INDWELLING INTRAVASCULAR APHAERETIC SYSTEM FOR IN VIVO ENRICHMENT OF CIRCULATING TUMOR CELLS

(71) Applicant: THE REGENTS OF THE UNIVERSITY OF MICHIGAN, Ann Arbor, MI (US)

(72) Inventors: Sunitha Nagrath, Ann Arbor, MI (US); Tae Hyun Kim, Pasadena, CA (US); Daniel F. Hayes, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 278 days.

(21) Appl. No.: 17/013,187

(22) Filed: Sep. 4, 2020

(65) Prior Publication Data
US 2021/0060229 A1    Mar. 4, 2021

Related U.S. Application Data

(60) Provisional application No. 62/895,773, filed on Sep. 4, 2019.

(51) Int. Cl.
*A61M 1/36*     (2006.01)
*A61K 31/727*   (2006.01)

(52) U.S. Cl.
CPC ........... *A61M 1/362* (2014.02); *A61K 31/727* (2013.01); *A61M 1/367* (2013.01);
(Continued)

(58) Field of Classification Search
CPC .... A61M 1/362; A61M 1/367; A61M 1/3672; A61M 2205/3303
See application file for complete search history.

(56) References Cited

U.S. PATENT DOCUMENTS 3,788,471 A * 1/1974 Buchmann ............. B01D 61/28
                                              210/321.89
3,791,767 A * 2/1974 Shill ..................... A61M 60/37
                                              604/153
(Continued)

FOREIGN PATENT DOCUMENTS

EP    1910572 A2    4/2008
EP    2995953 A1    3/2016

OTHER PUBLICATIONS

Klarhöfer M, Csapo B, Balassy C, Szeles JC, Moser E. High-resolution blood flow velocity measurements in the human finger. Magn Reson Med. Apr. 2001;45(4):716-9. doi: 10.1002/mrm.1096. PMID: 11284002. (Year: 2001).*

(Continued)

*Primary Examiner* — Nilay J Shah
(74) *Attorney, Agent, or Firm* — MARSHALL, GERSTEIN & BORUN LLP

(57) ABSTRACT

An apparatus for capturing circulating tumor cells (CTCs) from blood. The apparatus includes a wearable device that receives fluid from vasculature of a subject through an input channel. A pump is coupled to the input channel the pump configured to receive blood at a first flow rate and to convert the flow of the blood to a second flow rate. The device further includes a replaceable candidate cell capture module having a microfluidic capture stage with herringbone channel structures configured to capture the candidate cells by antibodies. The device is further configured to provide the blood back to the vasculature of the subject.

27 Claims, 12 Drawing Sheets

(52) U.S. Cl.
CPC ... *A61M 1/3672* (2013.01); *A61M 2205/3303* (2013.01); *A61M 2205/3306* (2013.01); *A61M 2205/3317* (2013.01); *A61M 2205/3334* (2013.01); *A61M 2205/3337* (2013.01); *A61M 2205/50* (2013.01); *A61M 2209/088* (2013.01)

(56) References Cited

U.S. PATENT DOCUMENTS

| | | | |
|---|---|---|---|
| 5,284,470 A * | 2/1994 | Beltz | A61M 1/3486 604/4.01 |
| 8,951,484 B2 | 2/2015 | Bersano-Begey et al. | |
| 9,090,865 B2 | 7/2015 | Di Carlo et al. | |
| 9,250,242 B2 | 2/2016 | Martin et al. | |
| 9,494,500 B2 | 11/2016 | Chang et al. | |
| 2003/0134416 A1 * | 7/2003 | Yamanishi | A61M 1/3679 435/372 |
| 2005/0284815 A1 * | 12/2005 | Sparks | A61M 1/1647 604/4.01 |
| 2010/0326916 A1 * | 12/2010 | Wrazel | A61M 1/16 210/205 |
| 2011/0244443 A1 * | 10/2011 | van Rijn | A61M 1/3403 435/283.1 |
| 2011/0294187 A1 * | 12/2011 | Toner | G01N 33/54366 435/177 |
| 2012/0063971 A1 | 3/2012 | Carlo et al. | |
| 2013/0255361 A1 | 10/2013 | Juncker et al. | |
| 2014/0113324 A1 | 4/2014 | Di Carlo et al. | |
| 2014/0224710 A1 | 8/2014 | Di Carlo et al. | |
| 2015/0285808 A1 * | 10/2015 | Nagrath | G01N 33/54366 435/7.23 |
| 2016/0077097 A1 | 3/2016 | Rao et al. | |

OTHER PUBLICATIONS

Stott, S. L., Hsu, C. H., Tsukrov, D. I., Yu, M., Miyamoto, D. T., Waltman, B. A., . . . & Toner, M. (2010). Isolation of circulating tumor cells using a microvortex-generating herringbone-chip. Proceedings of the National Academy of Sciences, 107(43), 18392-18397. (Year: 2010).*

Kim, et al.; "A temporary indwelling intravascular aphaeretic system for in vivo enrichment of circulating tumor cells;" Nature Communications https://doi.org/10.1038/s41467-019-9439-9 (2019).

Kim, et al.; "A temporary indwelling intravascular aphaeretic system for in vivo enrichment of circulating tumor cells;" Nature Communications https://doi.org/10.1038/s41467-019-9439-9 (2019). Supplementary Information.

Stott, Isolation of Circulating Tumor Cells Using a Microvortex-Generating Herringbone-Chip, Proceedings of the National Academy of Sciences, vol. 107, No. 43, pp. 18392-18397 (Oct. 26, 2010) (http://www.pnas.org/content/107/43/18392.full <https://protect-us.mimecast.com/s/qO6JBKTo7YluK>).

* cited by examiner

| CANINE ID | TYPE | WEIGHT [Kg] | MAX. # CELLS (TIME) | ACCUMULATED # OF CELL COUNT |
|---|---|---|---|---|
| D1 | BEAGLE | 12.1 | 90 (AT 30 min) | 356 |
| D2 | BEAGLE | 13.2 | 122 (AT 15 min) | 513 |
| D3 | BEAGLE | 13.2 | 134 (AT 15 min) | 596 |

* NUMBER OF MCF-7 CELLS INJECTED: $2 \times 10^7$ CELLS

INDWELLING INTRAVASCULAR APHAERETIC SYSTEM FOR IN VIVO ENRICHMENT OF CIRCULATING TUMOR CELLS

CROSS-REFERENCE TO RELATED APPLICATION

Priority is claimed to U.S. Provisional Patent Application No. 62/895,773, filed Sep. 4, 2019, the entire disclosure of which is incorporated herein by reference.

FIELD OF THE DISCLOSURE

The present disclosure relates to cancer cell related monitors and, more particularly, to a device for capturing circulating tumor cells.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Cancer metastases arise from circulating tumor cells (CTCs) that are shed from the primary tumor and circulate through lymphatic channels and blood. Although identified more than 150 years ago, until recently, CTCs were difficult to detect, enumerate, and characterize. Using modern technologies, several studies have now demonstrated that elevated levels of CTC isolated from a single blood draw may be biomarkers for patients with various carcinomas and are prognostic in patients with metastatic breast, colorectal, prostate, and lung cancers, as well as early stage breast and prostate cancers. Furthermore, CTC analysis holds promise for predicting benefit from targeted therapies, pharmacodynamic monitoring during treatment, and insight into the biology of metastases. Indeed, CTC evaluation might be used for early detection of malignancy, if an assay with sufficient sensitivity and specificity could be developed.

CTCs are extremely rare events. For example, in a single 7.5 mL tube of whole blood drawn from an average patient with metastatic breast cancer, it is unusual to identify more than 10 CTCs within the context of billions of erythrocytes and millions of leukocytes normally present. More than a hundred ex vivo CTC capture devices have been developed to enrich and isolate CTC from whole blood. However, CTC isolation using these technologies is limited to small blood volumes (usually 1-50 mL) due to patient safety concerns, and therefore the absolute number of CTC is small. Moreover, a single blood draw interrogates only those CTC present at the time of venipuncture, and does not take into account temporal differences in CTC release into the circulation. Current methods for interrogating CTCs result in statistical variability and inaccurate reflection of tumor cell heterogeneity. Generally speaking, there is a need for an ability to interrogate larger blood volumes over extended periods to enhance the number of CTCs available for enumeration, and thereby increase statistical confidence of sampling for comparison of serial levels. Doing so could also provide more CTCs for molecular phenotyping, genotyping, and further biological characterization.

Attempts to increase the volume of blood evaluated for CTC isolation have included using alternative sites of blood collection, including the vessels draining primary cancers accessed at the time of surgery. However, the accessibility to these sources is limited according to the location of the tumor, and this approach is not practical for routine diagnostic use. Furthermore, despite the considerable number of CTCs detected in samples from the tumor draining vessels, many cells that are disrupted during surgery rapidly undergo apoptosis, and their biological and clinical impact is unknown.

Other investigators have reported isolating CTC in cytopheresis products, either from whole blood or bone marrow, often collected in anticipation of hematopoeitic stem cell transplantation therapy. Although this strategy enables a substantial increase in detecting CTCs compared with a single blood draw, standard cytopheresis is cumbersome and inconvenient for the patient. Furthermore, cytopheresis products mainly consist of concentrated peripheral blood mononuclear cells, which require an additional high throughput screening step for CTC identification. As with cannulating tumor-draining vasculature, the logistics required for standard leukapheresis/cytopheresis render this approach impractical as a standard diagnostic test, especially for application in a serial fashion.

Investigators have also reported use of an intravenous gold-coated stainless steel medical wire with a hydrogel layer covalently coupled with antibodies against epithelial cellular adhesion molecule (EpCAM) protein (GILUPI Cell-Collector). However, physiologic variations between patients affecting blood flow and affinity make it difficult to standardize quantitative interpretation of CTCs by time of insertion. Similarly, a recent study has demonstrated in vivo capture of non-small cell lung cancer cells injected into a porcine model, using a flexible magnetic wire (MagWIRE). However, the approach requires pre-injection of EpCAM coated magnetic particles to label CTCs which limits its long-term application due to possible systemic exposure of iron overload.

There is a need for effective indwelling solutions for capturing CTCs with high efficiency.

SUMMARY

The present techniques address shortcomings of current CTC detection approaches, by providing a temporary indwelling, intravascular aphaeretic CTC isolation system that can be worn by a patient for several hours to several days, and through which a relatively large volume of blood can be interrogated. The devices and techniques herein may be implemented ex vivo or in vivo to capture CTCs or other candidate cells. More generally, the devices and techniques herein may be implemented to detect or capture any number of candidate targets beyond CTCs, examples include circulating tumor DNA (CTDNA), nucleic acids, viral particles, or bacterial particles.

In accordance with an example, a device for capturing circulating tumor cells from a carrier fluid, the device comprises: a housing having a fluid inlet channel and a fluid outlet channel, the housing having a receptacle engagement; a peristaltic pump encapsulated within the housing and fluidly coupled to the inlet channel to receive the carrier fluid at a first flow rate and configured to convert to a second flow rate and output the carrier fluid from a pump outlet channel at the second flow rate; a candidate cells capture module replaceably mounted to the receptacle engagement forming a fluidly sealed engagement between the candidate cells capture module and the housing, the candidate cells capture module having a microfluidic capture stage formed of one or more herringbone grooved capture channels to capture candidate cells, each herringbone grooved capture channels having an inverted notch in at least one herringbone switchback, the candidate cells capture module fluidly coupled to the fluid outlet channel; and an graphene oxide bonded antibody capture structure within the herringbone grooved capture channels to capture candidate cells within the carrier fluid. The housing may further include a heparin injector enclosed within the housing to prevent clotting.

Figure 1B:
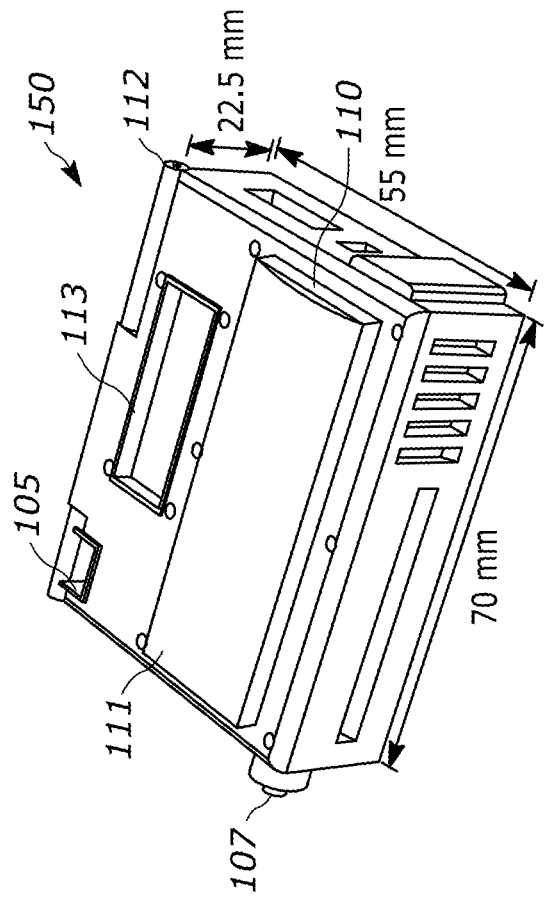
FIG. 1B is an illustration of a compact 3D printed structure for housing components of the system of FIG. 1A, in accordance with an example.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DESCRIPTION

Generally speaking, the present techniques describe temporary indwelling, intravascular aphaeretic candidate cell isolation systems. These systems may be worn by a patient for several hours to several days, in some examples. The systems are able to interrogate relatively large volumes of carrier fluid, such as blood, for capture candidate cells continuously within that carrier fluid. These systems may operate at normal patient blood flow rates allowing the system to collect blood from the patient and return blood to the patient, at normal blood flow rates, thereby creating an indwelling structure that may be worn by the patient over time. The systems described allow for interrogation of larger blood volumes than classic phlebotomy specimens over a prolonged period of time. The devices herein may be implemented ex vivo or in vivo to capture CTCs or other candidate cells and particles.

Figure 1A:
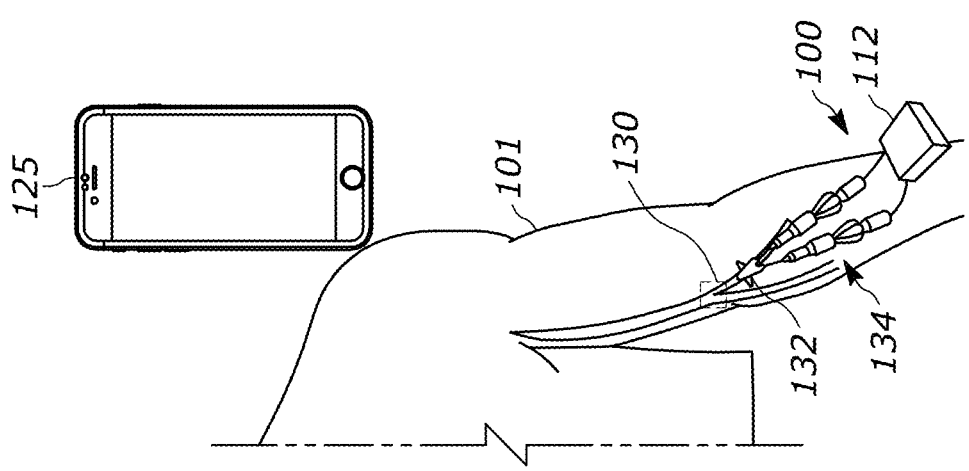
FIG. 1A is an illustration of an example system for performing in vivo detection of circulating tumor cells (CTCs), in accordance with an example.
Figure 1C:
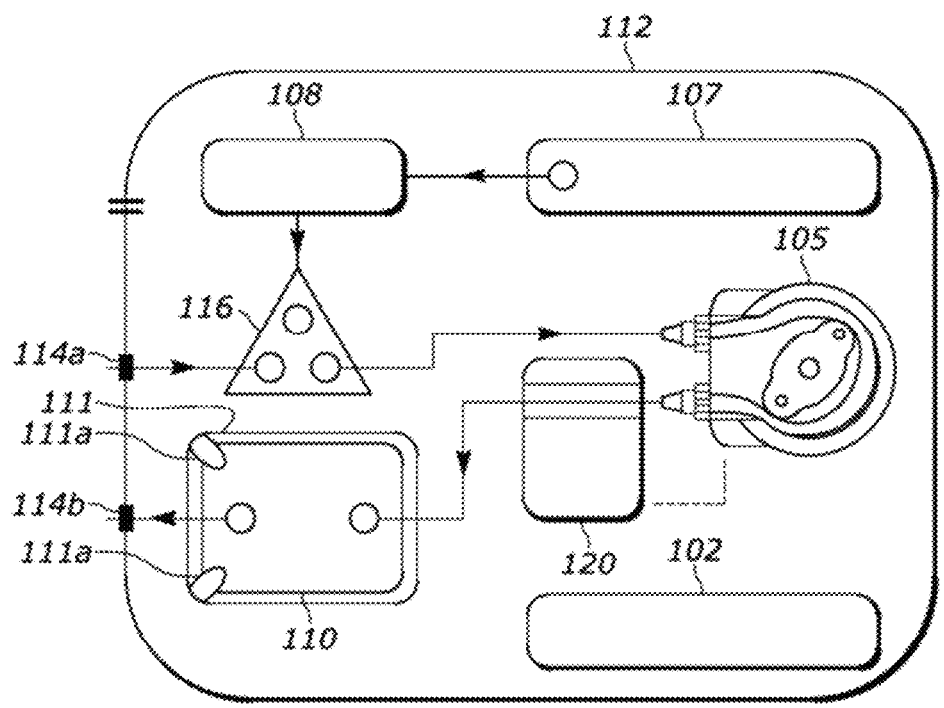
FIG. 1C is a schematic diagram of the system of FIG. 1A for performing in vivo detection of CTCs 100, in accordance with an example.

An overall design of an example system 100 of the techniques herein is illustrated in FIG. 1A. In the example system 100 of FIG. 1A, each functional component is integrated into a compact 3D printed structure 150, illustrated in example detail in FIGS. 1B and 1C. FIG. 1C is a schematic diagram of the system 100. The 3D printed structure 150 allows the system 100 to be portable enabling long term use of the system 100 by a subject 101 to interrogate larger volumes of carrier fluid of the subject 101.

The system 100 may be controlled through a custom built mobile application via wireless communication with a controller 125, also referred to herein as a control device. The controller 125 may be a cellular device, a tablet, a computer, a network, or another device in communication with the system 100 and capable of controlling the functionality of the system 100. In the illustrated example, the system 100 includes four main parts: a micro-controller 102, peristaltic pump 105, heparin injector 107, and a candidate cell capture module 110 (e.g., a CTC capture module). The capture module 110 contains a microfluidic capture stage in the form of a microfluidic capture chip, all encapsulated fully or partially within a housing 112. The system 100 is designed to accommodate any type of CTC isolation device, as long as it is configured to fit into the housing 112 or form part of the housing 112. The housing 112 may have a fluid inlet channel 114a and a fluid outlet channel 114b. Additionally, the housing 112 may be attachable to a wearable mount (e.g., a mount on a belt, wearable strap, article of clothing, glove, etc.) for releasable attaching of the housing 112 to an exterior of a patient. As such, a user of the system 100 may be mobile during operation of the system 100.

In embodiments, the housing 112 includes a receptacle engagement 111. The receptacle engagement 111 configured to physically couple to the candidate cell capture module 110 to hold the candidate cell capture module 110 in place. The receptacle engagement 111 may be configured to form a fluidly sealed engagement between the candidate cell capture module 110 and the housing 112. The candidate cell capture module 110 may couple to the receptacle engagement 111 in a manner that allows for removal of the candidate cell capture module 110 allowing for the replacement of one candidate cell capture module with a different candidate cell capture module. Therefore, the receptacle engagement 111 enables modular functionality of the candidate cell capture module 110 which may be desired to replace a defecting capture module, replace a saturated capture module, replace a capture module with a module having a different antibody or for detecting a different candidate, or for another reason for replacing one capture module with another capture module.

In embodiments, the receptacle engagement 111 may include a backplane or pocket on the housing 112 as illustrated in FIG. 1B. The candidate cell capture module 110 may be placed in a region supported by the backplane of the receptacle engagement 111 to position the candidate cell capture module 110 for operation of the system 100. FIG. 1C illustrates an example of a receptacle engagement 111 having clips 111a that clip onto the candidate cell capture module 110 to hold the candidate cell capture module 110 in place during operation of the system. In embodiments, the receptacle engagement 111 may include fasteners, clips, fastener bands (e.g., rub bands, elastic bands, etc.), a latch, a screw, a spring clamp, a vice, an adhesive, or another physical and/or mechanical structure to physically affix the candidate cell capture module 110 to the housing 112. Further, the receptacle engagement may include an O-ring, a fluid seal, a suction cup, a gasket, a labyrinth seal, an adhesive, a sealant, a plug, or another seal for forming a fluidly sealed engagement between the candidate cell capture module 110 and the housing 112. In any embodiment, the receptacle engagement 111 may provide a means for physically coupling the candidate cell capture module 110 to the housing 112.

In embodiments, the 3D printed structure 150 may include a region for a display 113. The display 113 may display information pertaining to a current operational status or current measurement of the system 100 (e.g., on, off, an error has occurred, a measurement of CTCs, a blood flow through the system 100, low battery, etc.). In embodiments, the display may include a light emitting diode display, a liquid crystal display, a touch screen, or another display capable of displaying alphanumerics or indicia indicative of a current status or measurement performed by the system 100. In embodiments, the controller 125 may control the display 113 to cause the display 113 to display information.

During example operation, whole blood is routed into the system 100 from a subject's peripheral vein 130 with a single cannulation 132 using a dual-lumen catheter 134 via the efflux lumen illustrated as the fluid inlet channel 114a. The fluid passes through a connector 116, a peristaltic pump 105, a flow rate sensor 120, and the CTC capture module 110. The fluid then exits the system 100 and flows back into the subject's circulatory system through the subject's vein 130 via the influx lumen of the catheter 134 labeled as the fluid outlet channel 114b. Each end of the catheter 134 is connected to a silicone tube, treated with anticoagulation reagents, with luer lock adaptors that thread into the peristaltic pump 105 and the CTC capture module 110 forming a closed loop structure. In operation, the blood flow may be driven by the peristaltic pump 105 with a preprogrammed flow rate and total processing volume. The flow rate sensor 120 monitors the blood flow and maintains a constant flow through by providing feedback information pertaining to the monitored blood flow to the pump 105 and/or the controller 125. The pump 105 may increase or decrease the rate of flow of the blood based on the information provided by the flow rate sensor 120. In embodiments, the controller 125 may increase or decrease the rate of flow of the blood based on the information provided by the flow rate sensor 120. In embodiments the pump 105 may be a gear pump, diaphragm pump, a plunger pump, piston pump, bellows pump, lobed pump, flexible-vane pump, nutating pump, peristaltic pump, a centrifugal pump, a diffuser pump, a volute pump, a propeller, a mixed-flow pump, a peripheral pump, or another pump capable of pumping fluid.

In embodiments, the pump 105 receives the fluid (e.g., blood) at a first flow rate and the pump 105 is configured to pump the fluid to convert the flow rate of the fluid to a second flow rate. In embodiments, the flow rate sensor 120 is configured to monitor the first flow rate of the fluid into the pump 105, and further, the flow rate sensor may be configured to control the heparin injector 107 to provide heparin to blood or another fluid according to the monitored first flow rate. The flow rate sensor may be configured to monitor the second flow rate and to control operation of the pump 105 based on the monitored second flow rate. In embodiments, the flow rate sensor 120 may be in communication with the controller 125 to provide the controller with measured flow rates and the controller 125 may control the system (e.g., the heparin injector 107 and the pump 105) according to the flow rates provided to the controller 125. A single flow rate sensor module may be implemented to measure both the first flow rate and second flow rate. While illustrated as being a single flow rate sensors, multiple flow rate sensors may also be configured to measure the first flow rate and/or second flow rate. In embodiments, the first and/or second flow rates may independently be between and including 1 and 50 µL/min, 20 and 100 µL/min, 100 and 200 µL/min, or greater than 200 µL/min. In embodiments, the first flow rate may be below a normal blood rate for a patient, which may be patient dependent based on an average blood flow rate of the patient.

To prevent blood clot formation during operation, in an example, an optional heparin may be continuously infused through a heparin injector 107. The heparin injector 107 may be a pump, actuator, or other device capable of pumping heparin through a check valve 108 and into the connector 116. The connector 116 operatively connects the heparin injector 107 to the fluid inlet channel 114a to provide heparin to the fluid entering through the fluid inlet channel 114a. The heparin may be combined with the blood at the connector 116 to prevent coagulation of the blood in the system 100.

Every unit (i.e., the connector 116, peristaltic pump 105, flow rate sensor 120, etc.) and channel in direct contact to the blood during sampling and re-transfusion is sterilized and individually inspected before use and disposed afterwards. To prevent microbial contamination, in an example, all disposable units within direct contact to the blood including the tubes, luer connectors, and syringes were sterilized using heat or ethylene oxide gas sterilization and packaged separately.

Figure 2A:
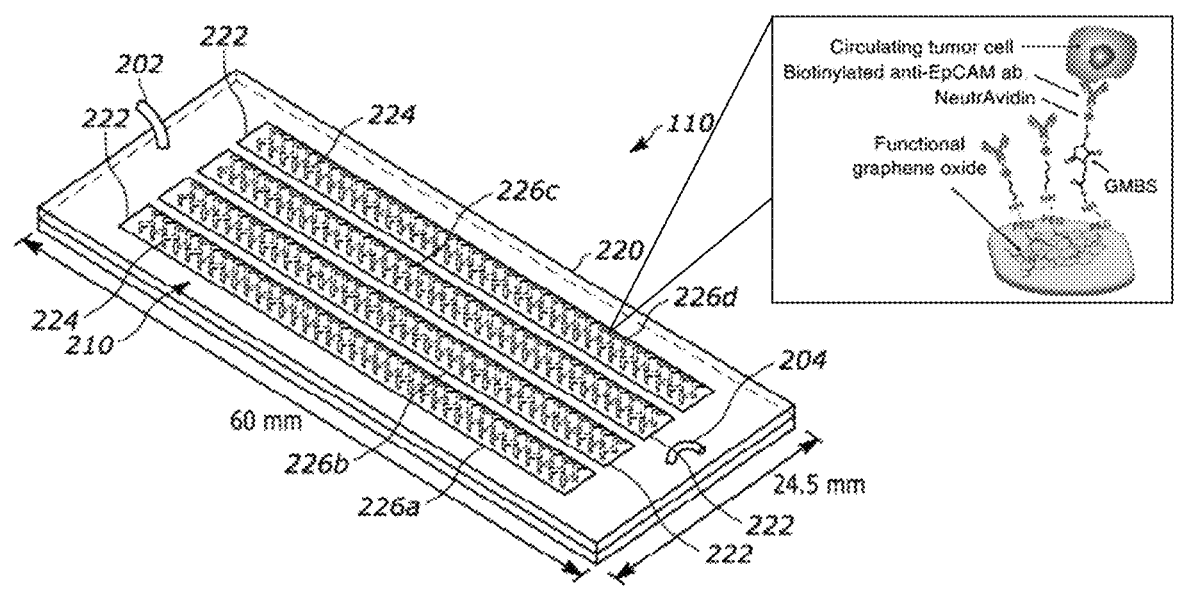
FIG. 2A illustrates of an embodiment of a CTC capture module including an inlet, an outlet, and a microfluidic capture stage, in accordance with an example.

FIG. 2A illustrates an embodiment of the CTC capture module 110. The CTC capture module 110 of FIG. 2A includes an inlet 202, an outlet 204, and a microfluidic capture stage 210. The capture module 110 may be replaceably mounted inside of the housing 112 and the capture module 110 may form a fluidly sealed engagement with the housing 112. The fluid enters the CTC capture module 110 through the inlet 202, the fluid passes through the microfluidic capture stage 210, and the fluid exits the CTC capture module 110 though the outlet 204. The outlet 204 of the microfluidic capture stage 210 may be in fluid communication with the fluid outlet channel 114b of the housing 112 to return the fluid to the vasculature of the patient. The microfluidic capture stage 210 includes a substrate that was exposed to UV, and a polydimethylsiloxane (PDMS) structure that was autoclaved before assembly of the microfluidic capture stage 210. All surface modification steps of the components of the microfluidic capture stage 210 were performed in a sterile, low germ count environment. In examples, the sterility of the devices and channels were measured by determining endotoxin levels using limulus-amebocyet-lysate (LAL) gel clot assay having 0.5 EU/mL sensitivity. The measurements resulted in no positive testing indicating that the endotoxin levels were less than 0.5 EU/ml. The measured endotoxin levels comply with current FDA guidelines of less than 0.5 EUmL for devices that directly or indirectly contact the cardiovascular system.

The PDMS structure and/or the substrate of the microfluidic capture stage 210 may be coated with gold and one or more reagents applied to the resultant gold structures to capture the CTCs. The reagents were sterilized and tested for endotoxin levels using LAL gel clot assay (0.5 EU/mL sensitivity, before the reagent was applied to the surface of the PDMS structure. Before operation of the CTC capture module 110, the microfluidic capture stage 210 was exposed to UV and fluid was exposed to the surface of the microfluidic capture stage 210. The fluid was then sampled, plated on sheep blood agar, and cultured for 2 weeks to detect any bacterial growth. While in an example EpCAM was used as a reagent to capture CTCs, other reagents may be used to capture other candidate cells. For example, CD31 may be used to capture enodethelial cells and miRNA may be captured using other reagents. Therefore, the microfluidic capture stage 210 may be configured to capture any of one or more types of candidate capture cells.

Figure 2B:
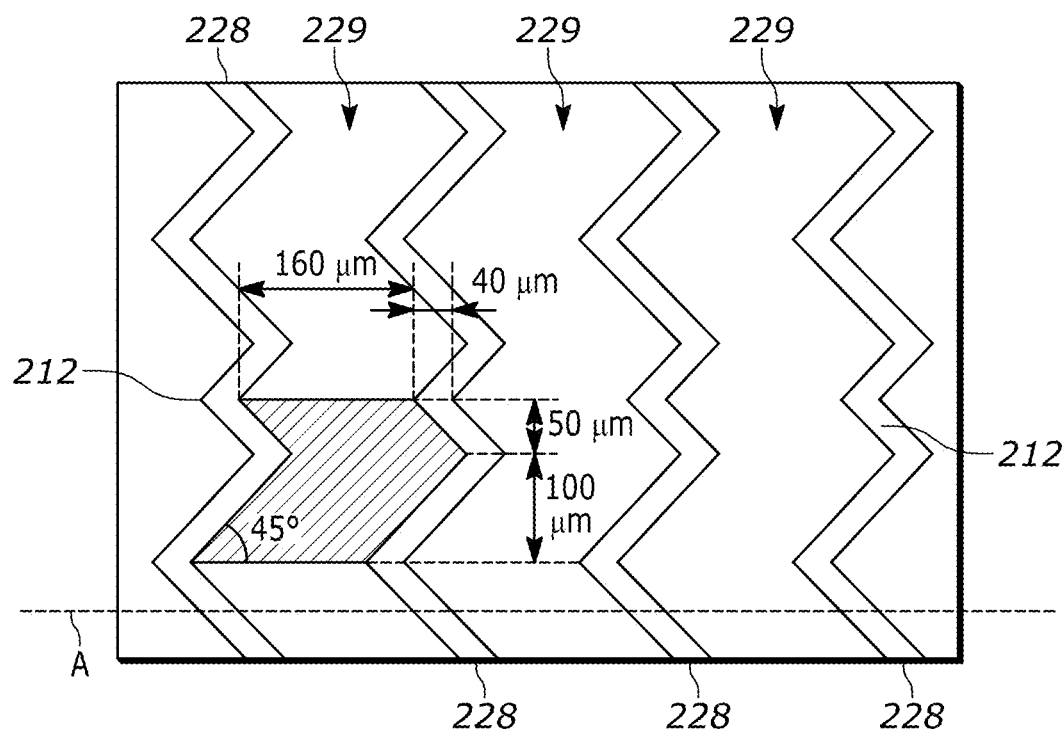
FIG. 2B is an illustration of an embodiment of herringbone channels of a microfluidic capture stage, in accordance with an example.
Figure 2C:
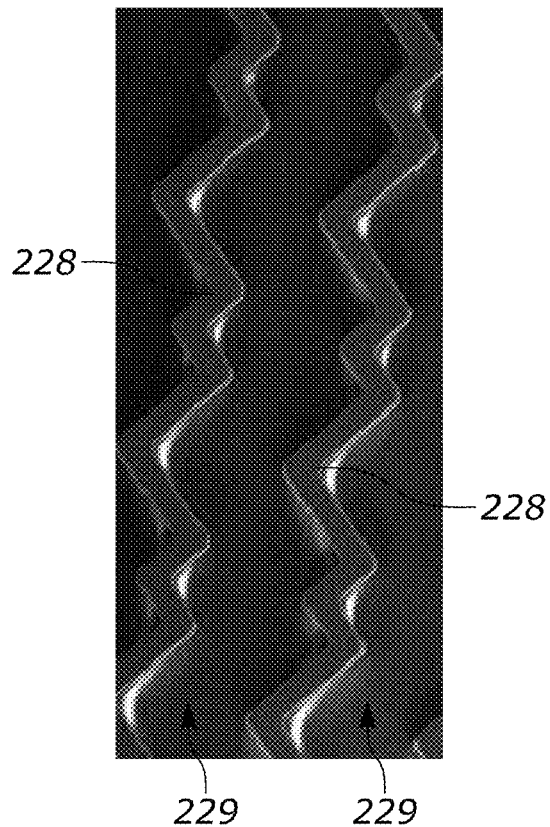
FIG. 2C is an image of an embodiment of herringbone channels of a microfluidic capture stage, in accordance with an example.
Figure 2D:
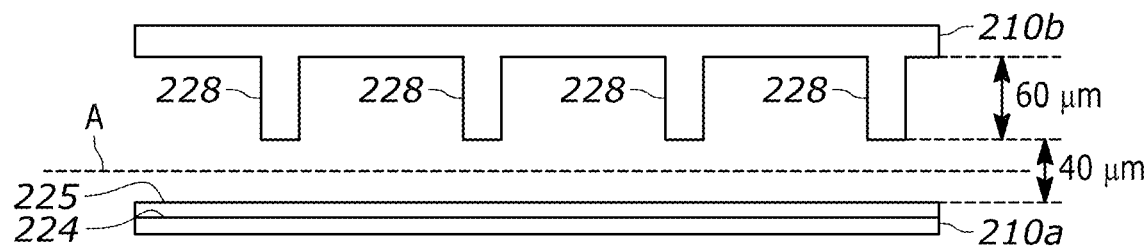
FIG. 2D illustrates a cross-sectional view of the channels of FIG. 2B, in accordance with an example.

FIGS. 2B and 2C are, respectively, an illustration and an image of an embodiment of channels of the microfluidic capture stage 210 of FIG. 2A. FIGS. 2D and 2F are illustrations of a cross-sectional view of the channels of FIG. 2B. In examples, the microfluidic capture stage 210 is a herringbone graphene oxide CTC chip, referred to herein as an HBGO chip. The HBGO chip may be designed using functional graphene oxide sheets for sensitive capture and chaotic mixing via herringbone structures for enhanced throughput. As illustrated in FIGS. 2B-2D, the microfluidic capture stage 210 may comprise a 24.5×60 mm silicon dioxide substrate 220 with a patterned gold thin film layer 224 bonded to a PDMS structure 222 containing four bifurcating microchannels 226a-226d. As illustrated in FIGS. 2D and 2F, the channels of the microfluidic capture stage 210 may include a bottom substrate 210a and a top substrate 210b. In embodiments, the bottom substrate 210a may be a same substrate as the substrate 220. Each of the microchannels 226a-226d may include herringbone structures 228 formed of the gold film on the top surface (i.e., the top substrate 210b) of each of the microchannels 226a-226d to form herringbone capture channels 229 between adjacent herringbone structures 228. As described herein, the herringbone capture channels 229 may be referred to as herringbone grooves or herringbone channels. In embodiments, the thin film gold layer 224 is applied to the bottom substrate 210a and functional graphene oxide nano sheets 225 may be assembled onto the gold thin film layer 224. The graphene oxide nano sheets 225 present high-density anti-EpCAM antibodies on the surface of the substrate 210a through chemical cross-linkers. The graphene oxide nano sheets 225 may include any antibody capture structure that is configured to capture candidate cells with the antibody being immobilized on the graphene oxide sheets 225 and extending from the graphene oxide sheets 225, as illustrated in the inset illustration of FIG. 2A. In embodiments, the candidate cell capturing antibody may include one or more of anti-EpCAM, CD133, EGFR, CD44, or another antibody. In embodiments, the candidate cells may include circulating tumor cells (CTCs), circulating tumor DNA (CTDNA), nucleic acids, viral particles, or bacterial particles. In embodiments, opposing outer walls of the herringbone capture channels 229 may be formed of PDMS.

The geometry of the herringbone structures 228 may be determined to cause chaotic mixing of a fluid flowing through the herringbone channels 229 at low Re number (i.e., Reynolds number). In embodiments, the herringbone structures 228 and herringbone channels 229 are configured to cause mixing of a fluid at an Re number of less than 100. The geometry of the herringbone structure may be modified to maximize the contact frequency of cells with the bottom substrate 210a where the antibodies are tethered, and therefore, where the CTCs are captured. The microfluidic capture stage 210 may be formed of one or more herringbone grooved capture channels 229 to capture candidate cells. Each herringbone grooved capture channel 229 may have an inverted notch 212 in at least one herringbone switchback (i.e., a chevron pattern). In some examples, the notches 212 are longitudinally aligned for each herringbone grooved capture channel 229. In some examples, fewer than all switchbacks have a notch 212 along a grooved capture channel 229. In some examples, every switchback has a notch 212. The herringbone capture channels 229 may be in parallel with one another, or the herringbone capture channels 229 may be offset from one another. In embodiments, the graphene oxide 225 may extend along the entire length of each of the herringbone capture channels 229, or the graphene oxide 225 may extend along a portion of the length of the herringbone capture channels 229. The herringbone structures 228 may extend from the bottom substrate 210a of the microfluidic capture stage 210 to the top substrate 210b of the microfluidic capture stage 210, extend from the top substrate 210b of the microfluidic capture stage 210 to the bottom substrate 210a of the microfluidic capture stage 210, or may extend partially from either of the top or bottom substrate 210a and 210b toward the corresponding other substrate of the microfluidic capture stage 210.

In an example embodiment, twenty-four chevrons, a set of twelve staggered asymmetrically, may be defined as a single mixing unit and periodically shifted along a channel axis A to place each vertex points with a spacing of 25 µm. A vertical (i.e., up and down in the plane of the page of FIG.

2D) drag force is induced by adjacent micro vortexes. The spatial distribution of the vertex points increases the probability of cells to be directed toward the antibody coated gold layer 224 covering the substrate. The dimension of the herringbone structure 228, such as the height, width, and pitch may be adjusted to decrease the hydraulic resistance past that of the main fluidic channel as compared to the hydraulic resistance of the vertical portion of the channel 229 having the herringbone structures 208. The height of the herringbone structure 228 may be measured from a surface from which the herringbone structures protrude, such as an inner surface of the top substrate 210b, shown in FIG. 2D. The main fluidic channel may be considered to be the vertical portion of the channel 229 unimpeded by the herringbone structures 228. The unbalanced resistance between the main fluidic channel and the portion of the channel 229 having the herringbone structures 228 increases the overall fluidic circulation by deflecting a significant portion of fluid and cells into the herringbone structure. The herringbone structure 228 may extend all the way to the button substrate 210a or, as shown, extend only partially to define the channel 229, where the amount of extension can affect channel operation and flow dynamics. In an example, the height to spacing gap ratio of the extending wishbone is 60 μm to 40 μm, that is with the herringbone height comprising 60% of the spacing gap between the top and bottom surfaces 210a and 210b. In the illustrated examples, the herringbone structures 228 have the same height. In other examples, the herringbone structures 228 may have different heights, for example, every even numbered herringbone structure 228 may have a first height and every odd numbered herringbone structure 228 may have a second height, when counting herringbone structures laterally along line A in FIGS. 2B and 2D.

Figure 2E:
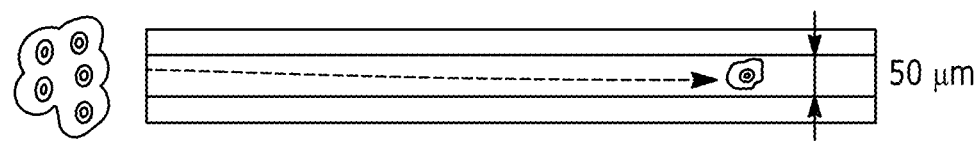
FIG. 2E illustrates a cell flowing through a flat microfluidic capture channel, in accordance with an example.
Figure 2F:
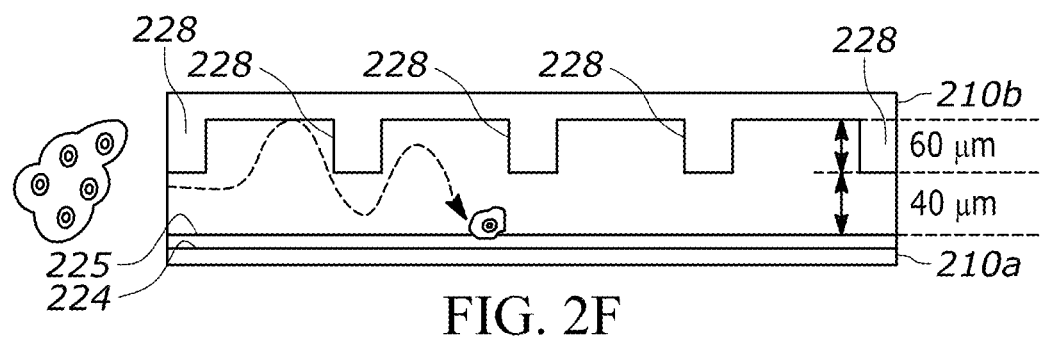
FIG. 2F illustrates a cell flowing through a herringbone microfluidic capture channel, in accordance with an example.

FIGS. 2E and 2F are respective illustrations of a cell flowing through a flat microfluidic capture channel and a herringbone microfluidic capture channel as described herein. Cells immersed and guided through the herringbone groove channels 228 move in a zigzag trajectory until captured, which increases the cells traveling time and travel distance within the microfluidic capture stage 210.

In embodiments, the micro-controller 102 may be configured to analyze candidate cells captured in the microfluidic capture stage 210. For example, the micro-controller may be configured to perform an optical analysis, visual inspection, automated counting, a microscopy technique, magnetic detection, electrical detection, or another form of detection of captured candidate cells. The micro-controller 102 may be configured to analyze the candidate cells in a herringbone grooved capture channel 229. In embodiments, the micro-controller 102 may include a memory that stores computer executable instructions that, when executed by the micro-controller 102 cause the micro-controller 102 to perform an analysis of captured cells.

EXAMPLES

Further details pertaining to preparing samples and performing tests according to the following examples are found in U.S. Provisional Patent Application No. 62/895,773, including the Appendices thereof, which is incorporated in entirety herein by reference.

Figure 3A:
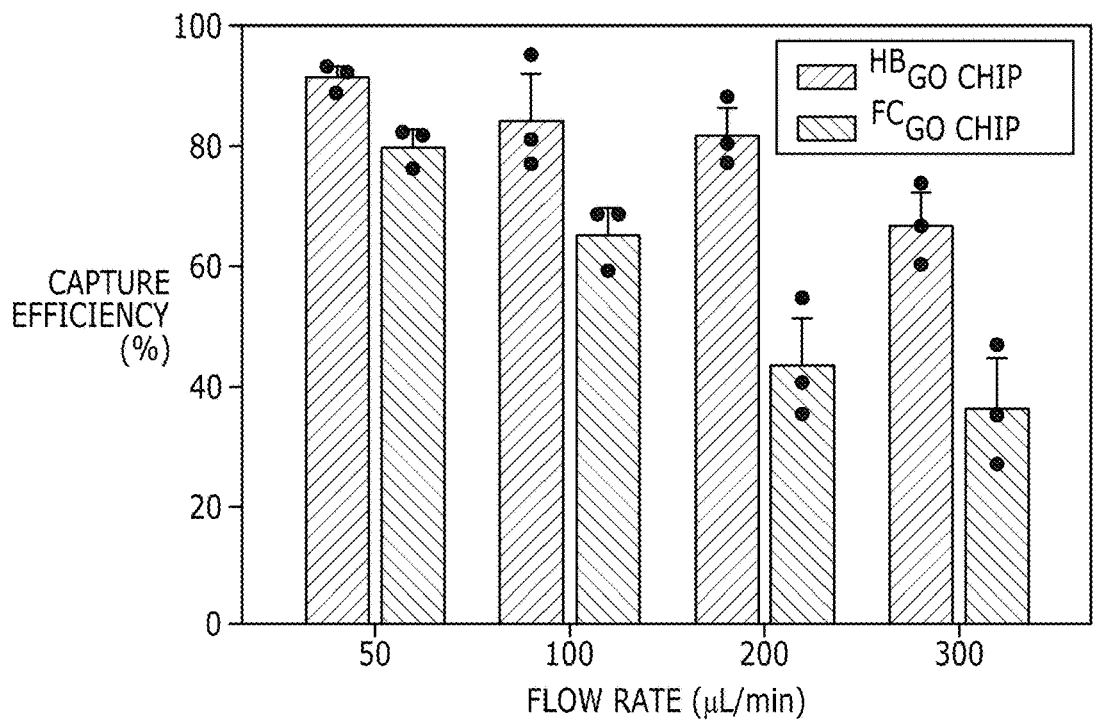
FIG. 3A is a bar graph of capture efficiencies for a flat microfluidic capture channel graphene oxide chip and a herringbone microfluidic capture channel graphene oxide chip, in accordance with an example.

In an example, the dimensions of the PDMS structure included a main fluidic channel height of 40 μm, a herring bone groove 229 height of 60 μm, herringbone groove 229 pitch of 200 microns, herringbone groove 229 width of 160 μm, and a 45° angle between chevrons, as illustrated in FIGS. 2B, 2D, and 2E. FIG. 3A is a bar graph of the capture efficiencies of a flat microfluidic capture channel graphene oxide chip (i.e., $^{FD}$GO chip), and a herringbone microfluidic capture channel graphene oxide chip (i.e., $^{HB}$GO chip) according to the example of FIGS. 2B, 2D, and 2E as described above. Culture human breast cancer MCF7 cells were labeled with a fluorescent cell-tracker dye and spiked into 5 mL of PBS buffer solution with a concentration of 50-200 cells/mL. Cells captured in the channels and non-captured cells collected into a waste well were counted to calculate the capture efficiency based on the total number of cells, and the number of cells captured. At a flow rate of 1 mL/h (~16.67 μL/min) (not shown in FIG. 3A), a range in which most affinity-based microfluidic devices operate, both the $^{FD}$GO chip and the $^{HB}$GO chip showed high capture efficiency with a mean yield above 90%. However, as shown in FIG. 3A, with increasing flow rates, the average cell capture efficiency for the $^{FC}$GO chip dropped below 80% at flow rates of 50 and 100 μL/min, and further decreased below 50% at 200 μL/min. In contrast, the $^{HB}$ GO chip maintained a capture efficiency of greater than 80% at flow rates up to 200 μL/min with no significant decrease in overall capture efficiency, indicating the effect of the disclosed herringbone channels for improved cell surface interaction and CTC detection. In embodiments, the herringbone groove capture channels 229 are configured to achieve a candidate capture yield of greater than 80% for a first flow rate of greater than 50 μL/min, greater than 100 μL/min, between 100 and 200 μL/min, or greater than 200 μL/min.

Figure 3B:
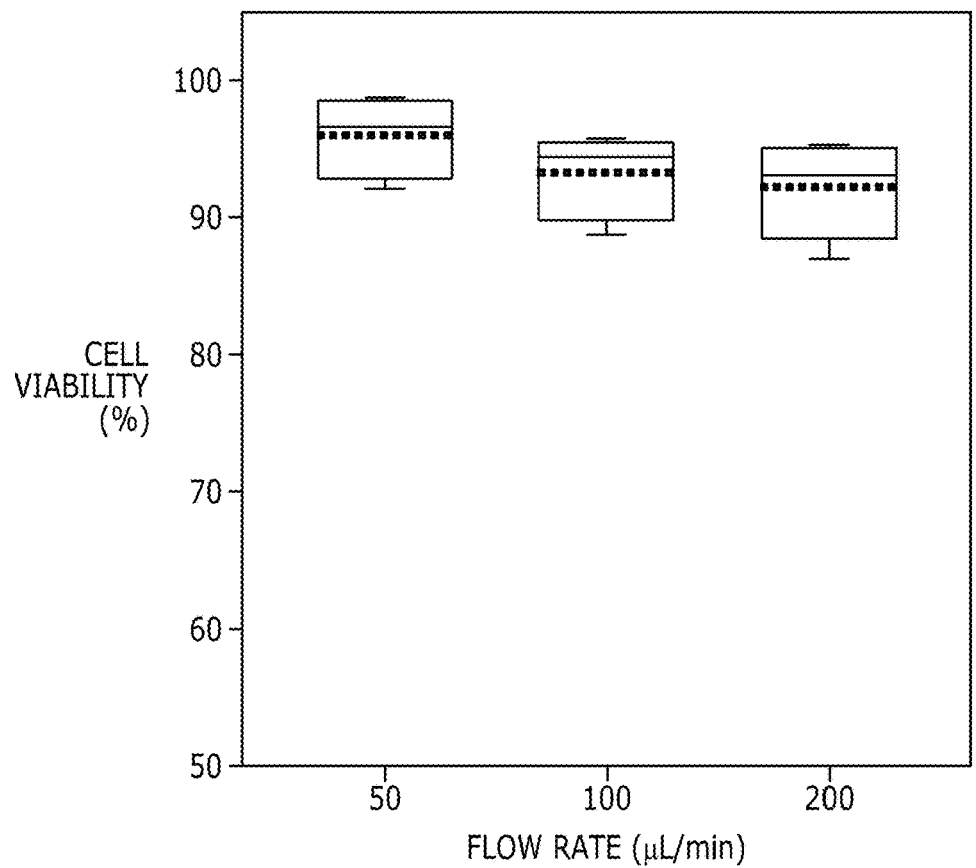
FIG. 3B is a plot of cell viability vs. flow rate for a herringbone microfluidic capture channel graphene oxide chip, in accordance with an example.

Cell viability was assessed at different flow rates to determine the effect of shear force induced by increasing flow rates during the isolation process. FIG. 3B is a plot of cell viability vs. flow rate for the $^{HB}$GO chip of FIGS. 2B, 2D, and 2E, and used for the measurements of capture efficiency of FIG. 3A. Cell viability may be critical as low cell viability may adversely affect further analysis of the isolated cells. Greater than 90% of the cells were found to be viable at flow rates of up to 200 μL/min with no significant reduction of viability compared with the viability at lower flow rates. The cell viability significantly decreased (i.e., reduced to less than 70%) at higher flow rates. Therefore, according to the current channel geometries of the $^{HB}$GO chip, flow rates greater than 200 are limiting factor of operation of the HBGO chip.

Figure 4:
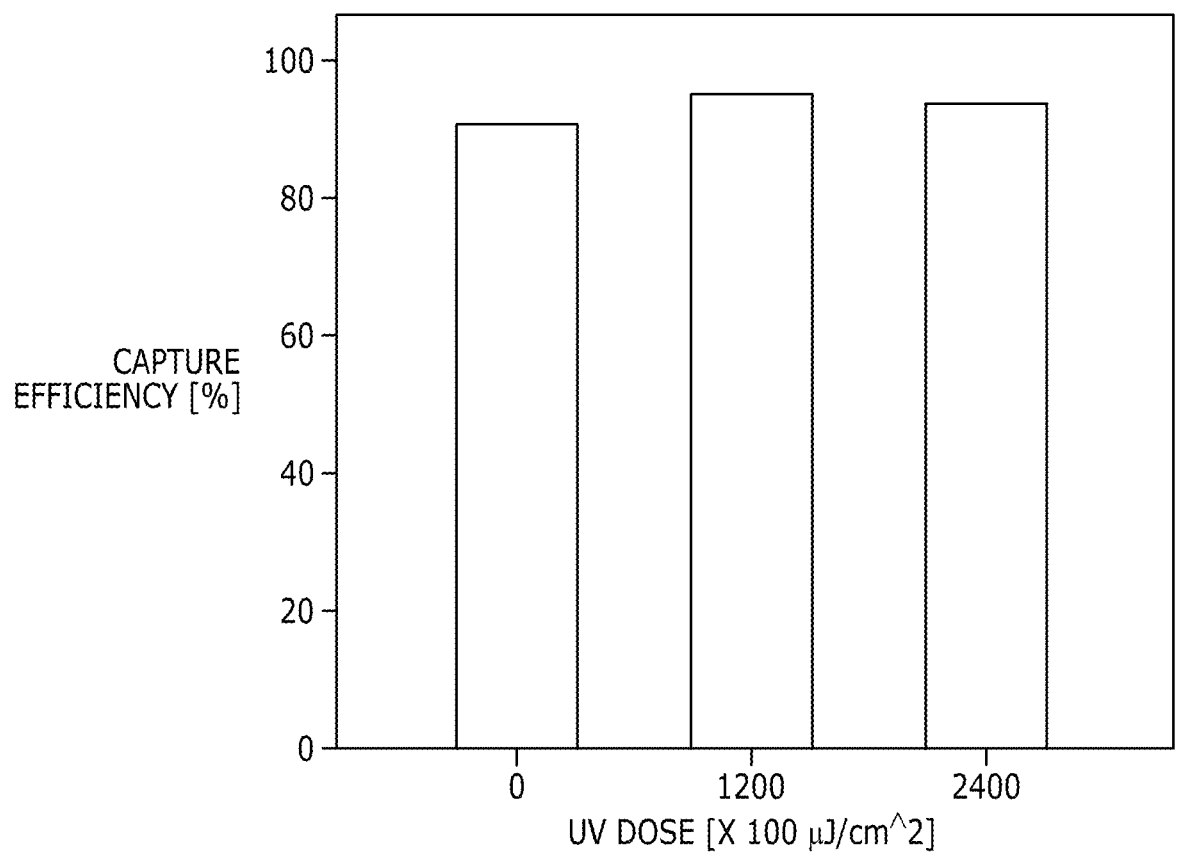
FIG. 4 is a plot of cell capture efficiency of an herringbone graphene oxide ($^{HB}$GO) chip after sterilization of the chip by varying doses of UV exposure, in accordance with an example.

FIG. 4 is a plot of capture efficiency of an $^{HB}$GO chip after sterilization of the chip by varying doses of UV exposure. The effect of UV radiation on chemical cross linkers and antibodies during the final sterilization process was determined. No adverse effect was observed in the cell capture performance of the UV exposed chips as compared to chips having no UV exposure. Additionally, the endotoxin levels of fluids obtained from the chips after sterilization were less than the 0.5 EU/mL detection limit. No bacterial growth was observed after blood was plated and cultured on sheep blood agar.

Figure 5:
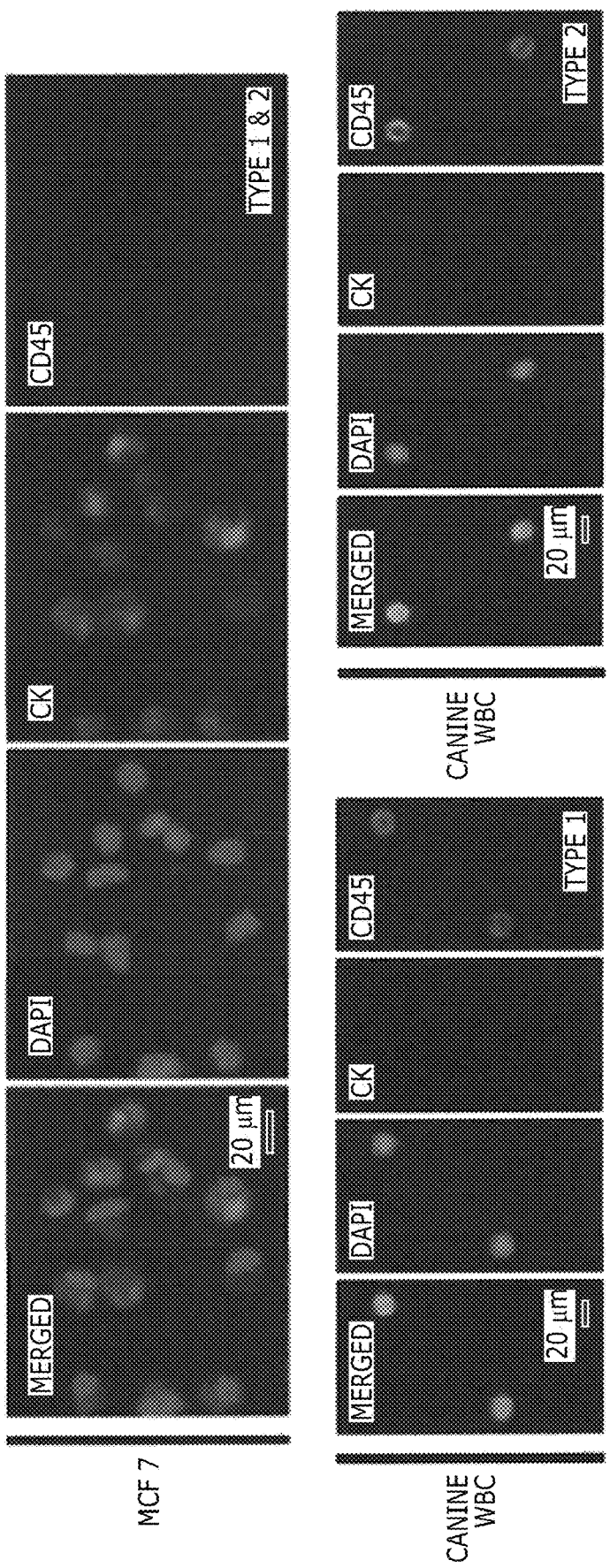
FIG. 5 shows a plurality of images of cells captured by the $^{HB}$GO chip having different stains to detect captured CTC cells, detect false positives, and to generate a merged image, in accordance with an example.

The disclosed system and methods for performing in vivo CTC capture was validated in canine models. Dogs were chosen over murine models, due to the larger vascular size and blood volume of dogs allowing more easy and reliable venous access. Also, dogs may represent a much more faithful model of human cancer. A total of 2×107 non-labeled MCF7 cells were injected into the dogs intravenously to mimic the natural occurrence of CTCs in blood. Peripheral blood was collected by venipuncture and the blood sampled before and after 1, 5, 15, 30, 60, and 120 min following injection to estimate the cell distribution during circulation and determine the optimal time interval for capturing candidate cells. The sampled blood was then processed through the $^{HB}$GO chip ex vivo at a flow rate of 100 μL/min. MCF7 cells captured by the $^{HB}$GO chip were quantified by positive CK staining with the absence of canine CD45. FIG. 5 shows a plurality of images of cells captured by the $^{HB}$GO chip having different stains to detect captured CTC cells, false positives, and to generate a merged image. CK staining from canine leukocytes was included in the measurements to account for false positives. The resultant captured cell count was subtracted from the cell count of the blood sampled before cell infusion. The captured cell count was then normalized to the maximum cell count from each test.

Figures 6A, 6B:
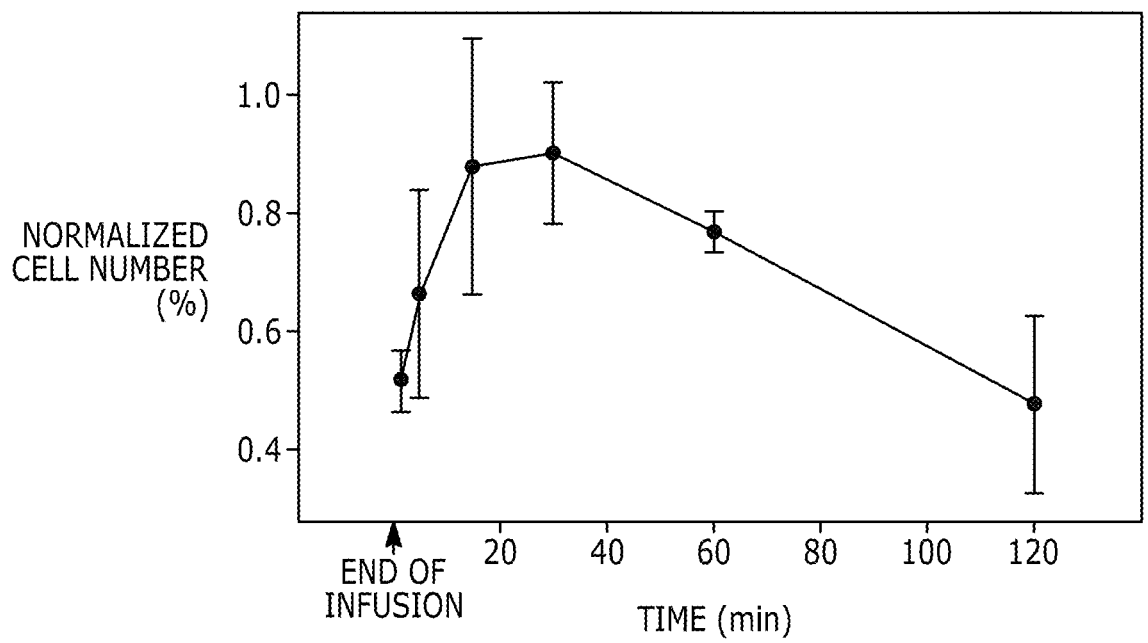
FIG. 6A is a plot of the normalized cell number of captured cells demonstrating the cellular kinetics of MCF7 cells after intravenous infusion, in accordance with an example.
FIG. 6B is a table of summarized results of the maximum cell count for serial blood draws and the accumulated cell count for three different animals, in accordance with an example
Figure 6C:
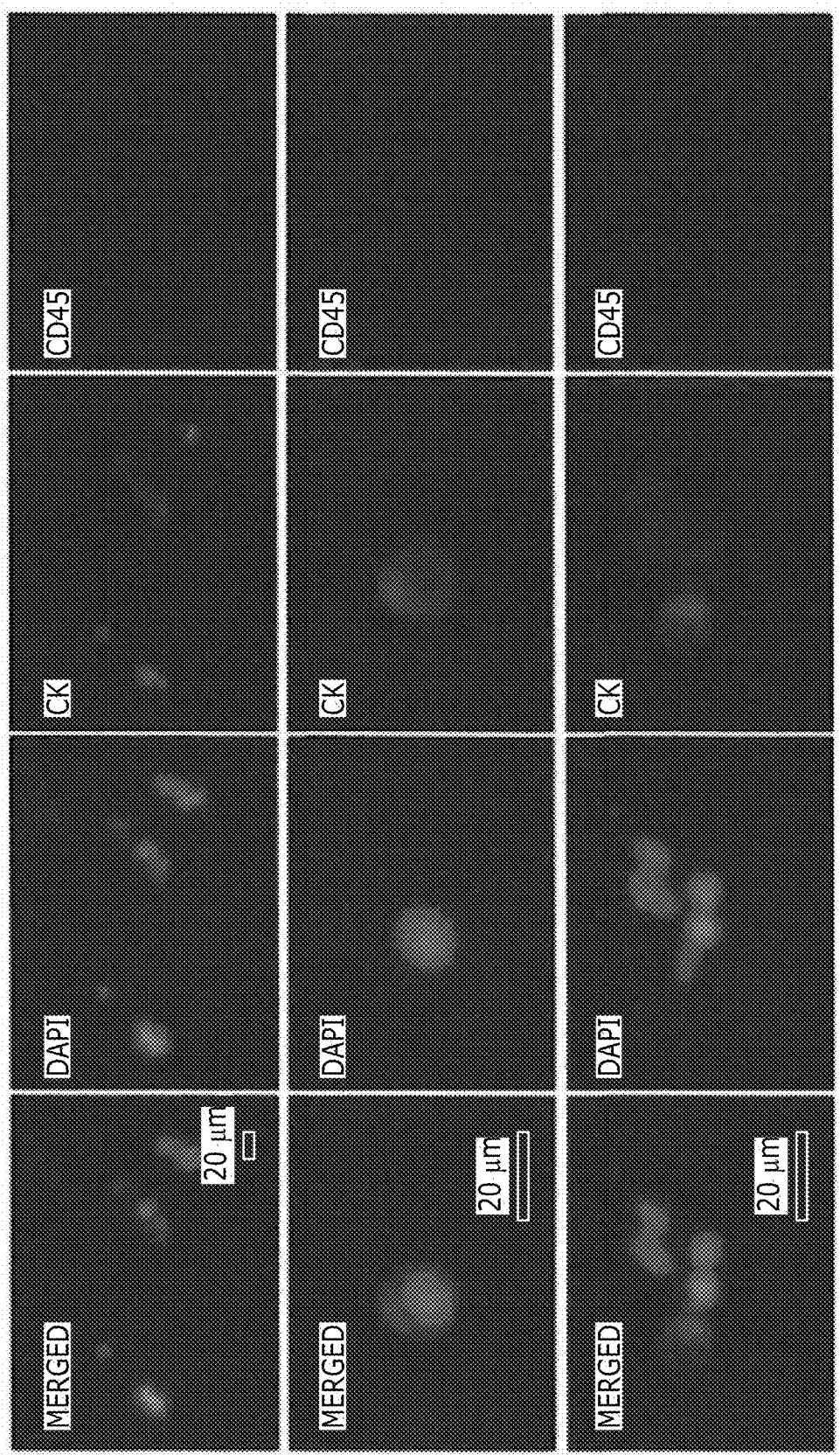
FIG. 6C is a plurality of images of cells and cell clusters having different fluorescent tags to generate a merged image for counting captured cells and cell clusters, in accordance with an example.

FIG. 6A is a plot of the normalized cell number of the captured cells which demonstrates the cellular kinetics of MCF7 cells after intravenous infusion. The data of FIG. 6A is averaged from intravenous infusion of MCF7 cells into three separate animals on different days. FIG. 6B is a table of summarized results of the maximum cell count for a serial blood draw at given time, and the accumulated cell count for the three different animals. The distribution time for cells to appear in circulation after injection was less than a minute. MCF7 cell counts rose to a maximum at 30 min from inoculation and declined over the succeeding 90 min due to cell clearance during circulation. Most MCF7 cells were identified as single cells but clusters were also detected. FIG. 6C is a plurality of images of cells and cell clusters having different fluorescent tags to generate a merged image for counting captured cells and cell clusters. Although the expression level of CK staining decreased as the time of blood sampling increased, MCF7 cells were detectable throughout the duration of the experimental duration of 2 hours. No short-term or long-term adverse effects from the MCF7 injection and venipuncture were observed in the animals.

In an example, an example implementation of the system 100 for detecting CTC cells was further tested for direct cell harvesting from in vivo circulation. The flow rate sensor 120 was removed from the system 100 as the flow rate sensor 120 was not disposable after use. The double-lumen catheter 134 was placed into the jugular vein of a dog, and blood was collected through the catheter 134 and provided to the $^{HB}$GO chip (i.e., CTC capture module 110) via pre-sterilized extension sets. The heparin injector 107 was connected to the check valve 108 configured to provide heparin to the blood at the connector 116. All fluid paths were primed with 1% heparin and connected to the catheter 134. Prior to cell injection, the system 100 was activated for 30 minutes to inspect for any blood clotting or clogging activity in any components of the system 100, in any tubes, or in any connector junctions. The heparin concentration was varied during operation and it was observed that a 10% concentration of heparin with a 1:5 volume ratio to blood induced no detectable blood clogs or clots. The heparin is mixed with the blood through the peristaltic motion of the pump 105, and the micro vortices generated within the $^{HB}$GO chip. The mixing due to the pump 105 and the vortices is gentle enough for efficient mixing of the heparin while not causing noticeably damage to the blood or cells contained in the fluid.

Figure 7A:
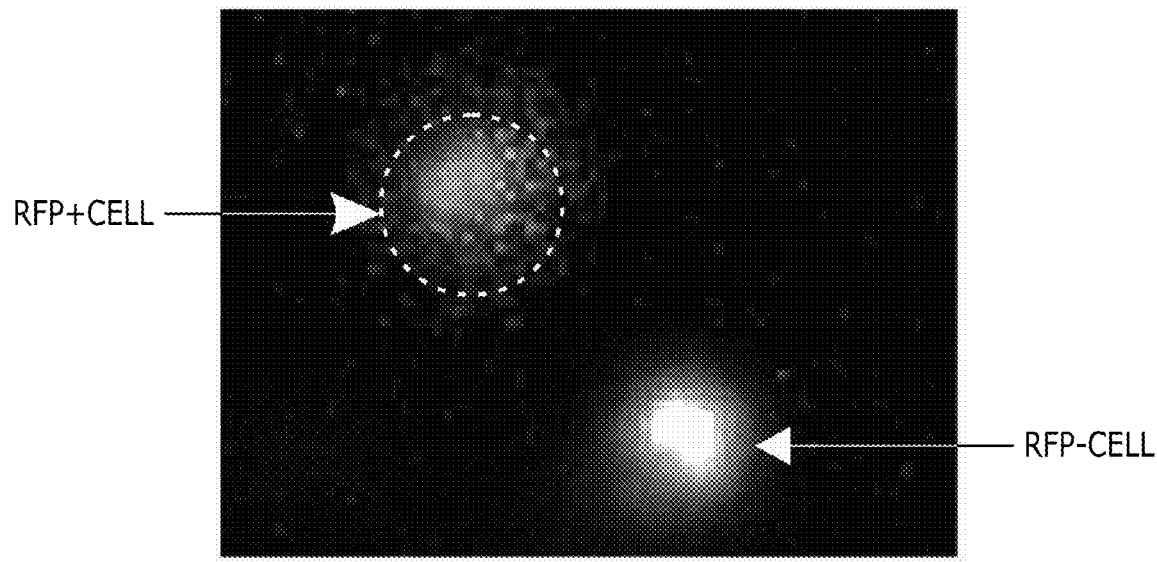
FIG. 7A is an image of captured CTC cell and a contaminating leukocyte, in accordance with an example.
Figure 7B:
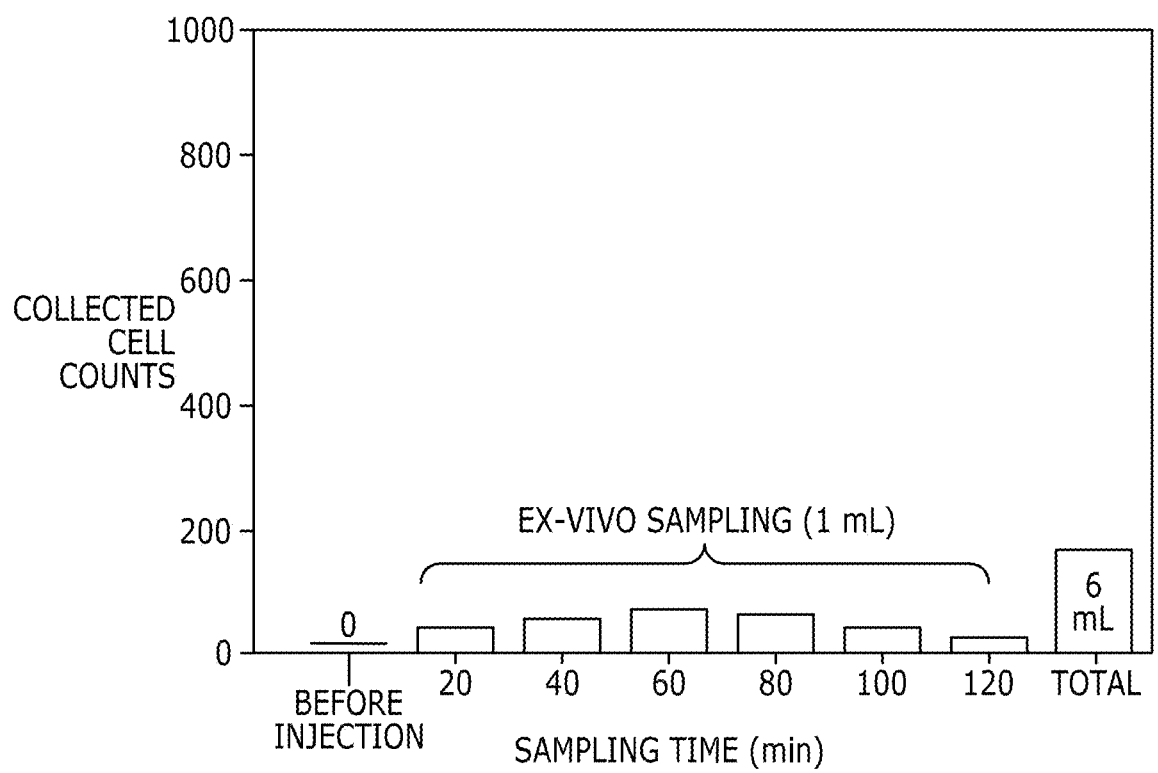
FIG. 7B is a bar graph of the number of cells captured ex vivo through the jugular vein of a test animal every 20 minutes, in accordance with an example.

After injection of the heparin, 2×107 red fluorescent protein (RFP) expressing MCF7 cells were injected into the cephalic vein of the canine subject and the system 100 was turned on 1 minute after the injection of the MCF7 cells. Blood was allowed to circulate through the device for up to 120 minutes. To compare and evaluate the performance of the system 100, 1 mL of blood was drawn, through the jugular catheter every 20 minutes, and analyzed for MCF7 presence by ex vivo CTC capture. FIG. 7A is an image of captured CTC cell and a contaminating leukocyte. The image of FIG. 7A illustrates the clear distinction between the RFP expression with, and without a captured CTC cell. FIG. 7B is a bar graph of the number of cells captured ex vivo through the jugular vein every 20 minutes. The average number of cells captured ex vivo for each draw of blood from the jugular vein was 35.33±8.46 cells/mL, with a maximum concentration of 45 cells/mL after 60 min. In total, 212 MCF7 cells were isolated and enumerated in the 6 mL of whole blood collected in 1 mL increments over the 2 hour period. As compared to the cell injection study described above in reference to FIGS. 6A-6C, the blood drawn from the jugular exhibited a slightly lower concentration of captured cells and a shift of time at which maximum concentration occurred, which is most likely due to the different physiological kinetics (e.g., differences in body size (7 kg), cardiac output, volumes of distribution, etc.) among the tested subjects of the two studies.

Figures 8, 9:
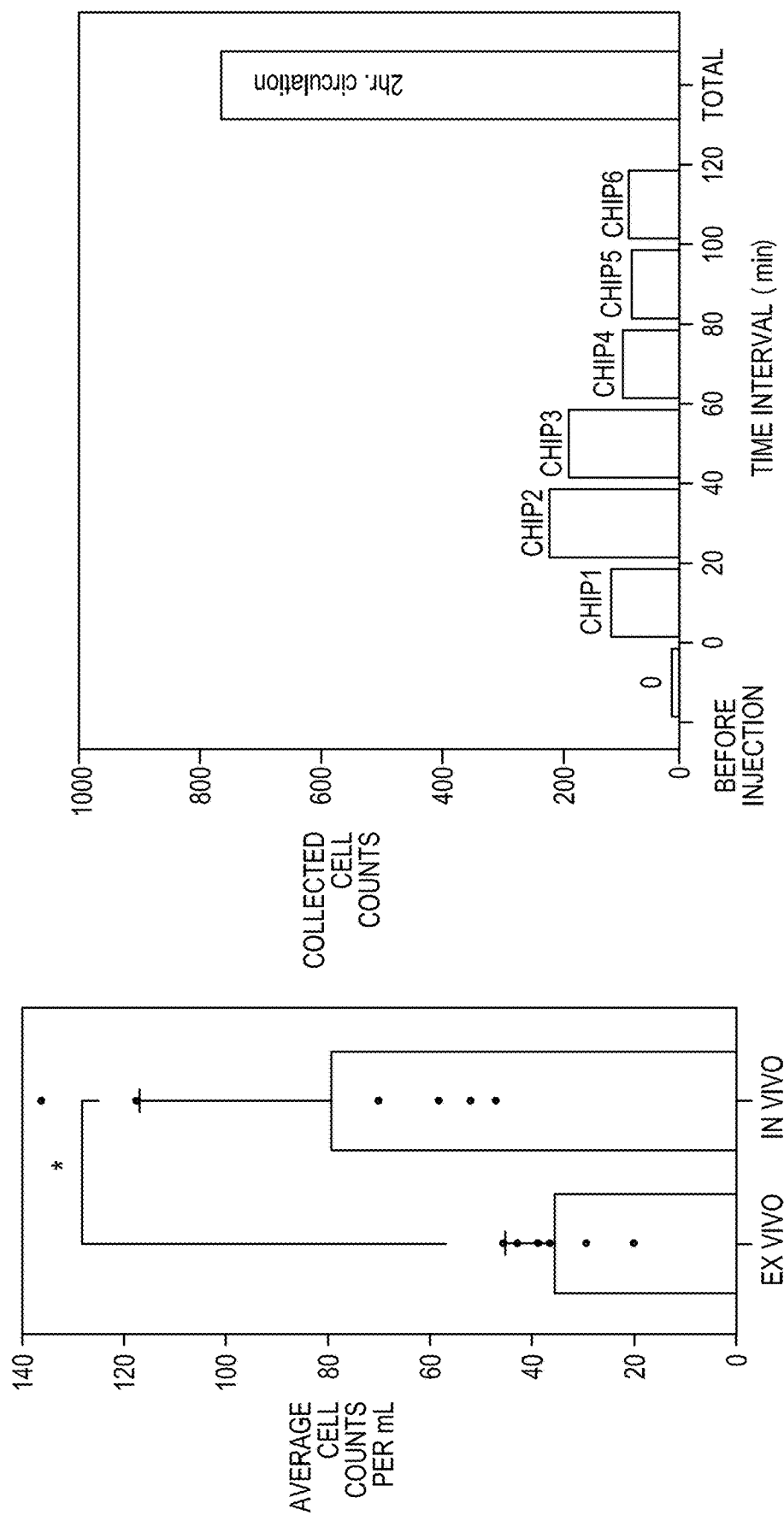
FIG. 8 is a bar graph of average cell count per milliliter captured for both ex vivo and in vivo cell capture measurements, in accordance with an example.
FIG. 9 is a bar graph of the collected cell count for 6 different $^{HB}$GO chips in a system with each chip being replaced by a subsequent chip every 20 minutes, in accordance with an example.

FIG. 8 is a bar graph of average cell count per milliliter captured for both the ex vivo and in vivo measurements described above. A total of 762 MCF7 cells were isolated in vivo over a period 2 hours by the indwelling intravascular CTC capture system described herein. The total capture of CTC in vivo by the indwelling system was approximately 3.5 times that of the periodic blood draw approach of FIGS. 7A and 7B illustrating that the disclosed system and method for capturing and detecting CTCs is more efficient and reliable than traditional methods. Additionally, the recovery rate measured as total number of cells per mL captured from in vivo circulation was substantially greater than recovery rate of the ex vivo capture method. The measurements described above show that discrete blood sampling at times after the predicted maximum cell concentration resulted in a lower recovery rate than the continuous intravenous isolation done in vivo. No RFP positive cells were identified in the blood obtained before cell infusion, confirming the specificity of the cell counts.

In embodiments, the surface of an $^{HB}$GO chip may become saturated with CTCs over a long period of time. Therefore, it may be beneficial to replace a saturated $^{HB}$ GO chip with a new unsaturated chip to capture CTCs without disrupting or interrupting the blood flow through the system 100. The current system 100 allows for replacement of HBGO chips for capturing CTCs while maintaining blood flow and sterility. The ability to replace chips during operation of the system 100 enables longer interrogation of an increased blood volume without having to discontinue the intravenous access. No visible interruption in blood flow was observed after swapping the chip every 20 min. FIG. 9 is a bar graph of the collected cell count for 6 different $^{HB}$GO chips in a system 100 with each chip being replaced by a subsequent chip every 20 minutes. As expected from the cellular kinetic data of FIG. 6A above, the CTC capture efficiency was greatest during operation of the second chip, which ran between the 20 to 40 min time period. Therefore, the systems and methods described herein may be useful for monitoring CTC counts in patients continuously for long periods of time such as tens of hours, or even days. There were no changes in clinical observations (i.e., temperature, pulse, respiration, body weight, food intake, etc.) or clinical pathology measurements (i.e., complete blood count, chemistry profile, coagulation, etc.) in any of the dogs at any time during or up to 7 days following any of the tests and procedures performed as described herein.

As described herein, the present techniques provide a temporary indwelling intravascular aphaeretic system that can enable long-term operation in vivo to continuously harvest large quantities of candidate cells, such as CTCs. The system re-transfuses the remaining blood products after the CTC isolation procedure, with minimal cell loss and minimal patient burden. Successful demonstration in canine models confirmed the feasibility of the described system for future interventional clinical studies. The canine models showed the capability to screen 1 to 2% of the entire blood of the canine over a two hour period. The flexibility of the disclosed system design can also be combined and adapted with various CTC enrichment methodologies or biochemical sensors that require real-time analytical information from the blood. Finally, high numbers of CTCs obtained from large volumes of blood screening will significantly reduce errors in determining the disease status and allow multiple characterizations of CTCs to gain insight into the molecular and functional role of CTCS, allowing for the realization of the full potential of liquid biopsy.

Beyond CTCs, as noted herein, the present techniques may be implemented on any number of target candidate circulating cells or molecules. These candidates include circulating tumor DNA (CTDNA), nucleic acids, viral particles, or bacterial particles. Candidates may include a cancer cell including malignant or benign circulating epithelial cells, endothelial cells, neurons, hepatocytes, nephrons, glial cells, muscle cells, skin cells, adipcytes, fibroblasts, chondrocytes, osteocytes, or osteoblasts. Candidate cells may include immune cells such as Natural Killer cells (NK cells), T cells, B cells and other Lymphocytes, macrophages. Candidates may include a cell expression including a marker of any of prostate cancer, lung cancer, adenocarcinoma, adenoma, adrenal cancer, basal cell carcinoma, bone cancer, brain cancer, breast cancer, bronchi cancer, cervical dysplasia, colon cancer, epidermoid carcinoma, Ewing's sarcoma, gallbladder cancer, gallstone tumor, giant cell tumor, glioblastoma multiforma, head cancer, hyperplasia, hyperplastic corneal nerve tumor, in situ carcinoma, intestinal ganglioneuroma, islet cell tumor, Kaposi's sarcoma, kidney cancer, larynx cancer, leiomyoma tumor, liver cancer, malignant carcinoid, malignant hypercalcemia, malignant melanomas, marfanoid habitus tumor, medullary carcinoma, metastatic skin carcinoma, mucosal neuromas, mycosis fungoide, neck cancer, neural tissue cancer, neuroblastoma, osteogenic sarcoma, osteosarcoma, ovarian tumor, pancreas cancer, parathyroid cancer, pheochromocytoma, primary brain tumor, rectum cancer, renal cell tumor, retinoblastoma, rhabdomyosarcoma, seminoma, skin cancer, small-cell lung tumor, soft tissue sarcoma, squamous cell carcinoma, stomach cancer, thyroid cancer, topical skin lesion, veticulum cell sarcoma, or Wilm's tumor. Circulating tumor DNA (ctDNA), i.e., DNA captured from cancer cells and tumors, may be found in the blood, for example, after cells are broken down. The techniques herein may thus be implemented using CTDNA compatible DNA affinity probes (e.g., DNA hybridization) to capture CTDNA in a carrier fluid, such as blood. Like CTC capture, capture of these other candidates can be used to reliably detect cancer and monitor tumor dynamics.

The devices herein may be deployed in a portable form factor to allow patients to carry or wear them with them throughout normal physical activity. In some examples, the devices are deployed in a wearable form factor, for example, where the housing of the capturing circulating tumor cells (or other target capture cells or molecules) device is mounted in a wearable structure that allows for releasable attaching to a patient. Such wearable structures include a removable band structure for attaching to an arm or leg of a patient or a removable patch structure for attaching to any number of locations on the body through a releasable adhesive.

Figure 10:
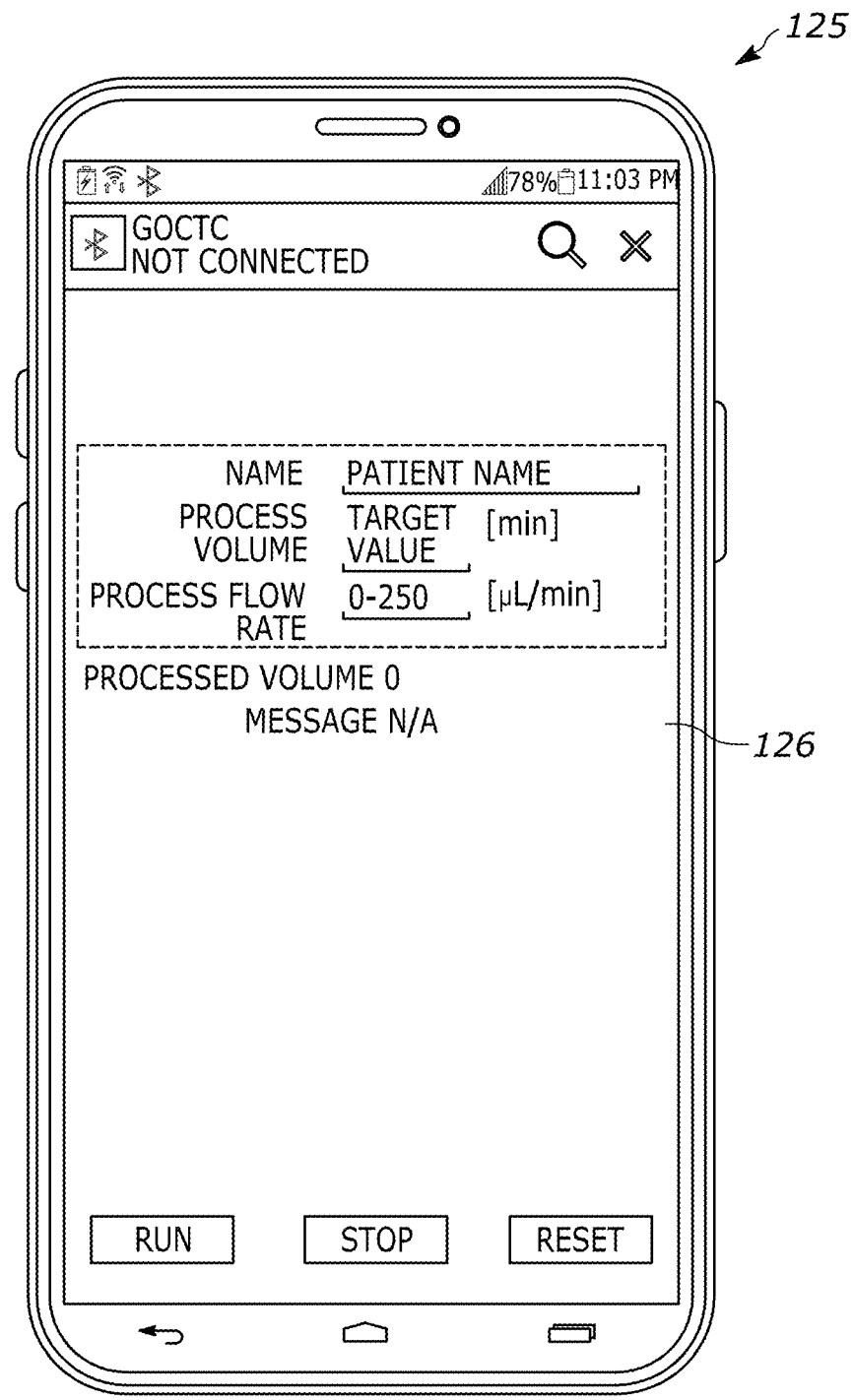
FIG. 10 is a schematic illustration of an example of a display provided by a user interface of a controller for controlling a system for performing in vivo detection of CTCs, in accordance with an example.

In embodiments, such as the embodiment of the system 100 of FIGS. 1A-1C, the controller 125 may control one or more operations of the system 100. For example, the controller 125 may be a portable device having a display screen and the controller may include a memory that stores machine readable instructions. The machine readable instructions may cause the controller 125 to display a user interface for a user to interact with for the user to provide commands to the system 100 by way of the controller 125. FIG. 10 is a schematic illustration of an example of a display provided by a user interface 126 of the controller 125. As illustrated in FIG. 10, the display screen may include fields for entering information such as a patient name, a desired amount of blood to process (i.e., process volume), a process flow rate, etc. Further, the interface 126 may provide to a user an option to run the system 100 according to the input parameters, and the interface 126 may provide the user an option to stop operation of the system 100. In embodiments, a user may use the stop function to pause operation of the system 100, or the interface may provide a user with a separate option to pause the operation of the system 100. The interface 126 may provide the user with an option to reset the parameters which may reset the processed volume to zero, clear error messages, and/or turn off the system 100 for the user to change out a chip of the system 100, or for the user to perform other maintenance of the system 100 or other physical operations. In embodiments, the controller 125 may store record data pertaining to a patient such as process volume for a given period of operation of the system 100, flow rate for a given operation of the system 100, number of sessions of operation of the system 100, total blood volume analyzed, number of CTCs detected, name of a patient, blood oxygen level, errors of the system 100, and other information indicative of operation of the system 100 and/or of the patient. In embodiments, the controller is configured to provide data to another computer or network to store data and/or provide data with another user or individual (e.g., a doctor or physician). In embodiments, the data may be provided by the controller to another computer or individual for further analysis of the data.

In embodiments, the controller 125 includes a communication module with the communication module being able to communicate with the system 100. The communication module may include a Bluetooth module that communicates with the system 100 to control the system. In embodiments, the communication module may include one or more communication chips or devices configurable to communicate with the system 100 via any suitable communication means, including wired and/or wireless connectivity components that implement one or more communication protocol standards like, for example, TCP/IP, WiFi (802.11b), Bluetooth, Ethernet, or any other suitable communication protocols or standards.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by size, space, cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A device for capturing circulating tumor cells from blood, the device comprising:
a housing having a fluid inlet channel and a fluid outlet channel, the housing having a receptacle engagement, the fluid inlet channel configured to receive the blood from vasculature of a subject and the fluid outlet channel configured to return the blood to the vasculature;
a peristaltic pump encapsulated within the housing and fluidly coupled to the inlet channel to receive the blood at a first flow rate and configured to convert to a second flow rate and output the blood from a pump outlet channel at the second flow rate;
a candidate cell capture module replaceably mounted to the receptacle engagement forming a fluidly sealed engagement between the candidate cell capture module and the housing, the candidate cell capture module having a microfluidic capture stage formed of one or more herringbone grooved capture channels to capture candidate cells, the one or more herringbone grooved capture channels protruding from a top substrate of the microfluidic capture stage, and the one or more herringbone grooved capture channels having a wall height that extends downward from a top surface of the top substrate at least 60% of a spacing gap between the top and a bottom surface of the microfluidic capture stage, the top surface of the top substrate defining a continuous upper bound extending from an inlet of the candidate cell capture module to an outlet of the candidate cell capture module and each of the one or more herringbone grooved capture channels having an inverted notch in at least one herringbone switchback, the inverted notch being a change of direction of the herringbone grooved capture channel between two adjacent peaks in the herringbone grooved capture channel, the candidate cell capture module fluidly coupled to the fluid outlet channel; and
a graphene oxide bonded antibody capture structure within the herringbone grooved capture channels to capture candidate cells within the blood, before the blood is returned to the vasculature through the fluid outlet channel.

2. The device of claim 1, wherein the microfluidic capture stage comprises a plurality of the herringbone grooved capture channels each in parallel to one another.

3. The device of claim 2, wherein the inverted notches of the herringbone grooved capture channels are longitudinally aligned to one another.

4. The device of claim 2, wherein each of the herringbone grooved capture channels has the inverted notch at each herringbone switchback.

5. The device of claim 2, wherein the graphene oxide of each of the herringbone grooved capture channels extends along a length of the herringbone grooved capture channel.

6. The device of claim 2, wherein each of the herringbone grooved capture channels are formed of a silicon dioxide substrate patterned with a gold film to form the herringbone grooved capture channels.

7. The device of claim 6, wherein opposing outer walls of the herringbone grooved capture channels are formed of polydimethylsiloxane (PDMS).

8. The device of claim 1, wherein the graphene oxide bonded antibody capture structure comprises a graphene oxide sheet having a candidate cells capturing antibody immobilized therein and extending therefrom.

9. The device of claim 8, where in the candidate cells capturing antibody is selected from the group consisting of anti-EpCAM, CD133, EGFR, and CD44, and the candidate cells are circulating tumor cells (CTCs), circulating tumor DNA (CTDNA), nucleic acids, viral particles, or bacterial particles.

10. The device of claim 1, wherein at least one herringbone grooved capture channel extends from a bottom substrate of the microfluidic capture stage to the top substrate of the microfluidic capture stage.

11. The device of claim 10, wherein the at least one herringbone grooved capture channel extends only partially from the bottom substrate of the microfluidic capture stage to a top substrate of the microfluidic capture stage.

12. The device of claim 1, further comprising:
a heparin injector encapsulated within the housing; and
a check valve connecting the heparin injector to the fluid inlet channel.

13. The device of claim 12, further comprising:
a flow rate sensor encapsulated within the housing, the flow rate sensor configured to monitor the first flow rate of the blood into the peristaltic pump and to control the heparin injector operation in injecting heparin into the blood upstream of the peristaltic pump, the flow rate sensor further configured to monitor and control operation of the second flow rate of blood from the peristaltic pump.

14. The device of claim 1, wherein the herringbone grooved capture channels have a fluidic channel height of 40 µm, a groove height of 60 µm, a groove pitch 200 µm, a groove width 160 µm, and an angle between chevrons of 45°.

15. The device of claim 1, wherein the herringbone grooved capture channels are configured to achieve a >80% candidate cells capture yield for first flow rates of greater than 1 mL/h (~16.67 µL/min).

16. The device of claim 1, wherein the herringbone grooved capture channels are configured to achieve a >80% candidate cells capture yield for first flow rates of greater than 50 µL/min.

17. The device of claim 1, wherein the herringbone grooved capture channels are configured to achieve a >80% candidate cells capture yield for first flow rates of greater than 100 µL/min.

18. The device of claim 1, wherein the herringbone grooved capture channels are configured to achieve a >80% candidate cells capture yield for first flow rates between 100 µL/min and 200 µL/min.

19. The device of claim 1, wherein the herringbone grooved capture channels are configured to achieve a >80% candidate cells capture yield for first flow rates greater than 200 µL/min.

20. The device of claim 1, wherein the first flow rate is at or below a normal blood flow rate for a patient.

21. The device of claim 1, wherein the candidate cells are circulating tumor cells (CTC), circulating tumor DNA (CTDNA), nucleic acids, viral particles, or bacterial particles.

22. The device of claim 1, wherein the candidate cells are cancer cells.

23. The device of claim 22, wherein the candidate cells are malignant or benign circulating epithelial cells, endothelial cells, neurons, hepatocytes, nephrons, glial cells, muscle cells, skin cells, adipocytes, fibroblasts, chondrocytes, osteocytes, or osteoblasts.

24. The device of claim 22, wherein the candidate cells are circulating immune cells, including at least one of Natural Killer cells (NK cells), T cells, B cells and other Lymphocytes, macrophages.

25. The device of claim 22, where the cancer cells express at least one marker of prostate cancer, lung cancer, adenocarcinoma, adenoma, adrenal cancer, basal cell carcinoma, bone cancer, brain cancer, breast cancer, bronchi cancer, cervical dysplasia, colon cancer, epidermoid carcinoma, Ewing's sarcoma, gallbladder cancer, gallstone tumor, giant cell tumor, glioblastoma multiforma, head cancer, hyperplasia, hyperplastic corneal nerve tumor, in situ carcinoma, intestinal ganglioneuroma, islet cell tumor, Kaposi's sarcoma, kidney cancer, larynx cancer, leiomyoma tumor, liver cancer, malignant carcinoid, malignant hypercalcemia, malignant melanomas, marfanoid habitus tumor, medullary carcinoma, metastatic skin carcinoma, mucosal neuromas, mycosis fungoide, neck cancer, neural tissue cancer, neuroblastoma, osteogenic sarcoma, osteosarcoma, ovarian tumor, pancreas cancer, parathyroid cancer, pheochromocytoma, primary brain tumor, rectum cancer, renal cell tumor, retinoblastoma, rhabdomyosarcoma, seminoma, skin cancer, small-cell lung tumor, soft tissue sarcoma, squamous cell carcinoma, stomach cancer, thyroid cancer, topical skin lesion, veticulum cell sarcoma, or Wilm's tumor.

26. The device of claim 1, further comprising a microcontroller detection stage configured to analyze candidate cells captured in the one or more herringbone grooved capture channels applying at least one of an optical analysis, visual inspection, automated counting, microscopy, magnetic detection, or electrical detection to the captured candidate cells.

27. The device of claim 1, wherein the housing is attached to a wearable mount for releasable attaching the housing to an exterior of the subject.

* * * * *

UNITED STATES PATENT AND TRADEMARK OFFICE
CERTIFICATE OF CORRECTION

| | |
|---|---|
| PATENT NO. | : 12,053,569 B2 |
| APPLICATION NO. | : 17/013187 |
| DATED | : August 6, 2024 |
| INVENTOR(S) | : Sunitha Nagrath et al. |

Page 1 of 1

It is certified that error appears in the above-identified patent and that said Letters Patent is hereby corrected as shown below:

In the Claims

At Column 18, Line 32, "200 µm," should be -- of 200 µm, --.

At Column 18, Line 33, "160 µm," should be -- of 160 µm, --.

At Column 20, Line 7, "veticulum cell sarcoma, or Wilm's tumor." should be -- reticulum cell sarcoma, or Wilms' tumor. --.

Signed and Sealed this
Fourth Day of February, 2025

Coke Morgan Stewart
*Acting Director of the United States Patent and Trademark Office*